(12) United States Patent
Socinski

(10) Patent No.: US 6,696,924 B1  
(45) Date of Patent: Feb. 24, 2004

(54) HAND-HELD APPARATUS FOR MONITORING DRUG-NUTRIENT-MINERAL INTERACTIONS AND METHOD THEREFOR

(76) Inventor: Tonia H Socinski, 54-F Starbird Rd., Jericho, VT (US) 05465

( * ) Notice: Subject to any disclaimer, the term of this patent is extended or adjusted under 35 U.S.C. 154(b) by 338 days.

(21) Appl. No.: 09/586,949

(22) Filed: Jun. 5, 2000

(51) Int. Cl.$^7$ ................................................. G08B 1/00

(52) U.S. Cl. .............................. 340/309.15; 340/309.4; 700/213; 700/233; 368/10; 221/2; 221/3; 221/15; 221/96

(58) Field of Search ......................... 340/309.15, 309.4; 368/10; 221/2, 3, 15, 96; 700/231, 233

(56) References Cited

U.S. PATENT DOCUMENTS

| | | | |
|---|---|---|---|
| 4,480,305 A | | 10/1984 | Watson et al. |
| 4,530,068 A | | 7/1985 | Nakanishi et al. |
| 5,408,443 A | * | 4/1995 | Weinberger .................. 368/10 |
| 5,609,268 A | * | 3/1997 | Shaw ............................ 221/2 |
| 5,612,869 A | * | 3/1997 | ILezt et al. .................. 395/203 |
| 5,646,912 A | * | 7/1997 | Cousin ........................ 368/10 |
| 5,673,691 A | * | 10/1997 | Abrams et al. ............. 128/630 |
| 5,825,675 A | | 10/1998 | Want et al. |

\* cited by examiner

Primary Examiner—Julie Lieu  
(74) Attorney, Agent, or Firm—Michael I Kroll (57) ABSTRACT

A hand-held device for alerting a user when scheduled medications, nutritional supplements, nutrients and minerals should be ingested. The device includes a processor positioned and a memory unit connected to the processor for storing user input data concerning a schedule for ingesting desired medications, nutritional supplements, nutrients and minerals. A display screen displays a message from the processor related to the schedule and function keys are connected to the processor for inputting the data concerning the schedule. The data includes a signal identifing the desired medications, nutritional supplements, nutrients and minerals to be ingested and a time at which they are to be ingested. The processor monitors a time of day and alerts the user when a scheduled time arrives. A speaker is connected to the processor for generating an audible alarm signal and alerting the user when a scheduled time arrives. The device is able to provide information concerning medications, nutritional supplements, nutrients and minerals as well as information concerning drug and nutritional supplement companies. The processor further monitors a schedule input by a user for taking medications, nutritional supplements, nutrients and minerals and alerts the user when the proper time arrives as well as checking to determine whether the user has scheduled times and dosages of medications, nutritional supplements, nutrients and minerals which may cause a harmful interaction. The user is also able to input personal daily, weekly, monthly schedules and schedule appointments or meetings.

15 Claims, 11 Drawing Sheets

HAND-HELD APPARATUS FOR MONITORING DRUG-NUTRIENT-MINERAL INTERACTIONS AND METHOD THEREFOR

BACKGROUND OF THE INVENTION

1. Field of the Invention

The present invention relates generally to hand-held computers and, more specifically, to a hand-held computer able to supply information to a user about allopathic and homeopathic drugs, nutrients and supplements, minerals and the effects of combinations thereof when taken together.

2. Description of the Prior Art

Numerous types of hand-held computers have been provided in the prior art. For example, U.S. Pat. Nos. 4,480,305; 4,530,068; 5,673,691 and 5,825,675 all are illustrative of such prior art.

U.S. Pat. No. 4,480,305

Inventor: Robert E. Watson

Issued: Oct. 30, 1984

A programmable calculator having modular read-write and read-only memory units, a central processing, a keyboard input unit, and an output display unit includes keys on the keyboard input unit for enabling the user to efficiently and effectively edit programs stored in the read-write memory unit.

U.S. Pat. No. 4,530,068

Inventor: Yasuhiro Nakanishi et al.

Issued: Jul. 16, 1985

An electronic hand-held memory device is capable of containing character information and numerical information stored together as a pair. Either or both types of information may be outputted, and the numerical information may be used for calculation. Loading and fetching of character information are performed upon actuation of keys. The desired key in effect acts as a memory key during a numeral information calculation mode. The desired key may serve as a constant memory key or a memory total key. When printing an output is desirable, the beginning of the character information is aligned with the most significant digit position and the end of the numerical information is aligned with the least significant digit position of a printer.

U.S. Pat. No. 5,673,691

Inventor: Philip S. Abrams et al.

Issued: Oct. 7, 1997

In the preferred embodiment, a hand-held computer prepares and monitors a goal-oriented weight, nutrition and exercise control program. Visual and audio prompts tell users when to eat and exercise, and provide suggestions for what to eat. The computer assists the user in setting safe goals for desired weight loss and the time required to achieve the loss. The user follows menu and exercise programs suggested by the computer. The computer records and analyzes the user's food consumption, exercise and weight loss programs. Finally, the computer displays feedback information regarding the users' progress towards achieving the desired weight.

U.S. Pat. No. 5,825,675

Inventor: Roy Want

Issued: Oct. 20, 1998

A hand-held computer having symmetrically placed buttons on one side so that left or right handed operation by the grasping hand is easily achieved. The hand-held computer includes a configuration method so that the functions of buttons and the orientation of images on the display screen can be adjusted for left or right handed use of the computer. Stylus input is modified by button presses thereby allowing more flexibility in inputting information to the computer. The computer includes rounded buttons as an aid to holding and operating the computer so as to improve operator comfort.

While these units may be suitable for the particular purpose to which they address, they would not be as suitable for the purposes of the present invention as heretofore described. None of these devices are able to provide a portable hand-held reference for drug-nutrient-mineral interaction for a user to determine the effects of taking certain medications with certain minerals and nutrients. Such effects include side effects and possible side effects from interactions between the drugs, nutrients and minerals. Furthermore, none of these devices provide user interactive feedback and reminders as to when prescribed medication and nutrients should be taken.

It is thus desirable to provide a hand-held device able to provide a user with information concerning the effects and interactions of certain nutrients and minerals with medication the user is currently taking. It is further desirable to provide a hand-held device able to remind a user when it is time to take prescribed medication, nutrients and minerals. It is still further desirable to provide a hand-held device which is interactive with a user to ensure that the prescribed medication and nutrients are taken at predetermined times and recording the results of the user interaction to determine when the user has and has not taken the prescribed medication and nutrients. It is even further desirable to provide a hand-held device which is not burdensome or obtrusive to the user and thus easy to carry around. It is yet further desirable to provide a hand-held device which is programmable for storing a schedule for a user indicative of the time and dosage of medication and nutrients to be taken by the user. It is still further desirable to provide a hand-held device able to warn a user as to possible interactions between any nutrients, drugs and minerals. It is even further desirable to provide a hand-held device able to provide a user with information concerning the manufacturers of nutrients, drugs and minerals to be taken thereby.

SUMMARY OF THE PRESENT INVENTION

The present invention relates generally to hand-held computers and, more specifically, to a hand-held computer able to supply information to a user about allopathic and homeopathic drugs, nutritional supplements, nutrients, minerals and the effects of combinations thereof when taken together.

A primary object of the present invention is to provide a hand-held computer that will overcome the shortcomings of prior art devices.

Another object of the present invention is to provide a hand-held computer which is able to store information regarding known allopathic and homeopathic pharmaceutical drugs, individual effects, clinical pharmacology, clinical studies, contraindications; warnings, precautions, adverse reactions, dosages; administration; how supplied, animal toxicology; patient information, properties, recommendations for use and effects when combined with nutritional supplements, minerals and nutrients, this information being provided to a user on demand.

A further object of the present invention is to provide a hand-held computer which is able to store information concerning interactive nutrients found in food products, nutritional supplements and minerals and providing such information to a user on demand.

A yet further object of the present invention is to provide a hand-held computer wherein medical and nutritional information concerning individuals may be stored for use in forming a nutritional and drug profile for the individual.

A still further object of the present invention is to provide a hand-held computer including a processor able to analyze the drug and nutritional information with respect to medical information concerning individual patients in order to provide a user with alternative drug, nutrient or mineral recommendations.

An even further object of the present invention is to provide a hand-held computer wherein the memory is also able to store information concerning producers and manufacturers of allopathic and homeopathic drugs, nutritional supplements and minerals.

Another object of the present invention is to provide a hand-held computer including a peripheral input port for connecting a peripheral device and thereby updating information stored in the memory.

A still further object of the present invention is to provide a hand-held computer including a second peripheral port for connecting with a printer or other output device and producing a hard copy of information provided to a user.

An even further object of the present invention is to provide a hand-held computer including a database of known pharmaceutical and homeopathic drug companies, a listing of their respective drugs and a description of each drug, the description of each drug including its generic name, common indications and usage, clinical pharmacology, clinical studies, contraindications; warnings, precautions, adverse reactions, dosages; administration; how supplied, animal toxicology; patient information, cautions, side effects and any nutrient or mineral interactions.

A yet further object of the present invention is to provide a hand-held computer including a database of known nutritional supplement companies, their respective supplements and a description of each supplement, the description including cautions regarding the supplement, side effects and any drug interactions.

Another further object of the present invention is to provide a hand-held computer including a complete database of nutrients and minerals and the recommended daily intakes for men, women and children for each.

A still further object of the present invention is to provide a hand-held computer including a drug and nutrient-mineral interaction program for providing the user with the best possible information regarding the interactions of any drug with any nutrient or mineral.

A yet further object of the present invention is to provide a hand-held computer that is simple and easy to use.

A still further object of the present invention is to provide a hand-held computer that is economical in cost to manufacture.

Additional objects of the present invention will appear as the description proceeds.

A hand-held device for alerting a user when scheduled medication, nutritional supplements, and minerals should be ingested is disclosed by the present invention. The device includes a processor positioned and a memory unit connected to the processor for storing user input data concerning a schedule for ingesting desired medication, nutritional supplements, minerals and nutrients. A display screen displays a message from the processor related to the schedule and function keys are connected to the processor for inputting the data concerning the schedule. The data includes a signal identifying the desired medication, nutritional supplements, minerals and nutrients to be ingested and a time at which they are to be ingested. The processor monitors a time of day and alerts the user when a scheduled time arrives. A speaker is connected to the processor for generating an audible alarm signal and alerting the user when a scheduled time arrives. The device is able to provide information concerning medications, nutritional supplements, minerals and nutrients as well as information concerning drug and nutritional supplement companies. The processor further monitors a schedule input by a user for taking medication, nutritional supplements, minerals and nutrients and alerts the user when the proper time arrives as well as checking to determine whether the user has the proper scheduled times and dosages of medications, nutritional supplements, minerals and nutrients to avoid any harmful interactions.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

DESCRIPTION OF THE REFERENCED NUMERALS

Turning now descriptively to the drawings, in which similar reference characters denote similar elements throughout the several views, the Figures illustrate the hand-held computer of the present invention. With regard to the reference numerals used, the following numbering is used throughout the various drawing figures.

10 hand-held computer of the present invention
12 top side of hand-held computer
14 bottom side of hand-held computer
16 display
18 allopathic prescription drug information key
20 nutritional supplement information key
21 help key
22 homeopathic drug information key
24 mineral and nutrient information key
26 numeric calculator keys
28 patient medical record information number key
30 drug company information key
32 nutritional supplement company information key
34 alphanumeric keyboard
36 power on key
38 power off key
40 hinges for closing hand-held computer
41 function key
42 outside housing
43 search key
44 lock/clasp
45 set/store key
46 left side of housing
48 first peripheral device port
50 second peripheral device port
52 right side of housing
54 speaker
56 recommended daily intake key
58 processor
60 power source
62 memory
64 keyboard keys
66 timer
68 enter key

DETAILED DESCRIPTION OF THE PREFERRED EMBODIMENT

Turning now descriptively to the drawings, in which similar reference characters denote similar elements throughout the several views, FIGS. 1 through 5 illustrate the hand-held computer of the present invention indicated generally by the numeral 10.

Figure 1:
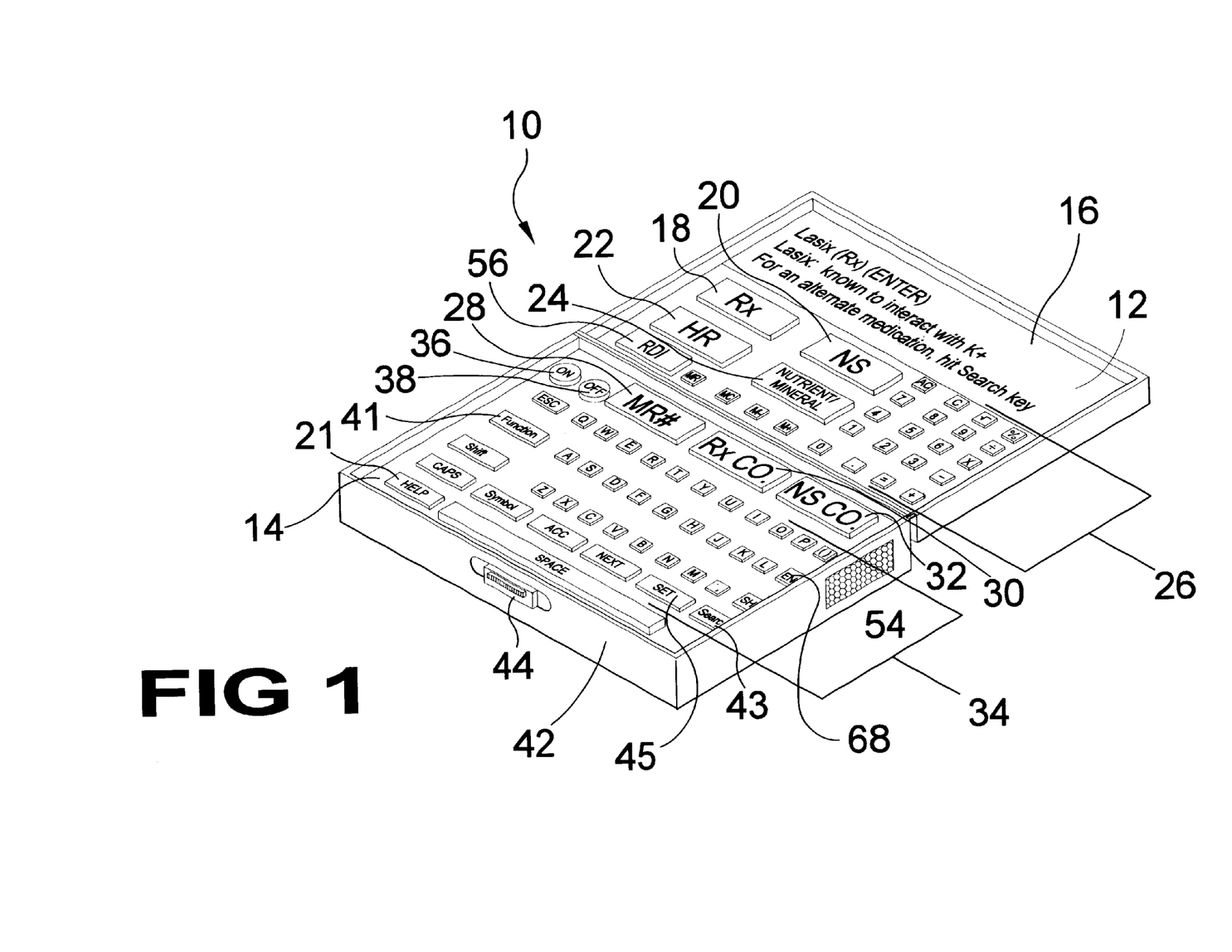
FIG. 1 is a top perspective view of the hand-held computer of the present invention in an open position.

The hand-held computer 10 is shown generally in an open position in FIG. 1. From this view the top side 12 and bottom side 14 of the hand-held computer 10 can be seen. Both the top side 12 and the bottom side 14 include a plurality of function keys which are exposed when the hand-held computer 10 is placed in the open position. The hand-held computer 10 may be placed in a closed position by pivoting the top side 12 to cover the bottom side 14 thereby preventing access to the function keys.

Positioned on the top side 12 is a display screen 16 along with a plurality of function keys. The display screen 16 displays information retrieved from the hand-held computer 10, application menus for aiding the user in retrieving and inputting information, the current date and time, and a cursor prompt for use in inputting information. Information displayed on the display screen preferably remains visible until additional information is retrieved, input or the hand-held computer 10 is turned off. The plurality of function keys include an allopathic prescription drug information key 1 8, a nutritional supplement information key 20, a homeopathic drug information key 22 and a mineral/nutrient information key 24. The allopathic prescription drug information key 18 provides information concerning allopathic prescription drugs and interactions of an allopathic drug with other drugs, minerals and supplements/nutrients. The nutritional supplement information key 20 provides information on nutritional supplements drugs and interactions of a nutritional supplement with other nutritional supplements/nutrients, minerals and drugs. The homeopathic drug information key 22 provides information on homeopathic drugs and interactions of a homeopathic drug with other drugs, minerals and supplements/nutrients. The mineral/nutrient information key 24 provides information on nutrients and interactions of a nutrient with other nutrients, drugs, minerals and supplements. Number and mathematical function keys 26 are provided on the top side 12 for use in inputting dosage amounts and performing mathematical calculations. Also positioned on the top side 12 is a RDI key 56. The RDI key 56 is provided for obtaining information stored within the hand-held computer 10 regarding the recommended daily intakes of desired minerals or nutrients.

The bottom side 14 of the hand-held computer 10 also includes a plurality of keys. Among the keys provided on the bottom side 14 of the hand-held computer 10 are a patient medical record key 28, a drug company key 30 and a nutritional supplement company key 32. An alpha-numeric keyboard 34 is also provided on the bottom side 14. The medical record key 28 is used to enter a mode in which a patient's medical record can be viewed. Upon activation of the medical record key 28, the user is prompted to enter the name or medical record number of the patient using the alphanumeric keyboard 34 having a medical record stored in the hand-held computer 10 and desired to be viewed. The prescription/drug company key 30 is used to obtain information of a desired drug company. Upon activation of the drug company key 30, the user is prompted to enter the name of the drug company using the alphanumeric keyboard 34 for which information is desired. The nutritional supplement company key 32 is used to obtain information of a desired nutritional supplement company. Upon activation of the nutritional supplement company key 32, the user is prompted to enter the name of the nutritional supplement company for which information is desired on the alphanumeric keyboard 34. A help key 21 is also provided on the bottom side 14 for assisting the user in programming and using the hand-held computer 10. An on button 36 and an off button 38 are provided for turning the hand-held computer 10 between an on and off power state. A function key 41 is provided for editing, deleting or copying information displayed on the display screen 16. A search key 43 is provided for searching for information on a specific patient, mineral/nutrient, drug etc. A set/store key 45 is provided for storing information into memory.

The positioning of the function keys on the top side 12 and bottom side 14 of the hand-held computer 10 are shown and described for purposes of example only. The function keys may be positioned in any desired manner on the hand-held computer 10 without affecting the operation thereof. The scope of the present invention is therefore not intended to be limited by the position of the function keys as illustrated in the drawings and described in the specification.

On an outer side of the hand-held computer 10 is a speaker 54. The speaker 54 provides audible signals to the user. These audible signals include an audible alarm signal for alerting the user when it is time to take medication, nutritional supplements or nutrients, minerals and homeopathic medicine. The speaker 54 also creates an audible alarm signal to alert the user when any combination of medication, nutritional supplements, homeopathic medicine or minerals/nutrients may cause an adverse reaction. Also audiblized through the speaker 54 are messages of encouragement and support to the user. The messages of encouragement and support are designed to provide positive reinforcement to the user for following the schedule set for ingestion of medication, nutritional supplements, minerals and homeopathic medicine. A clasp 44 is also provided on an outer side of the hand-held computer 10 for locking the top and bottom sides 12 and 14, respectively, together in a closed position restricting access to the display screen 16 and the function keys.

Figure 2:
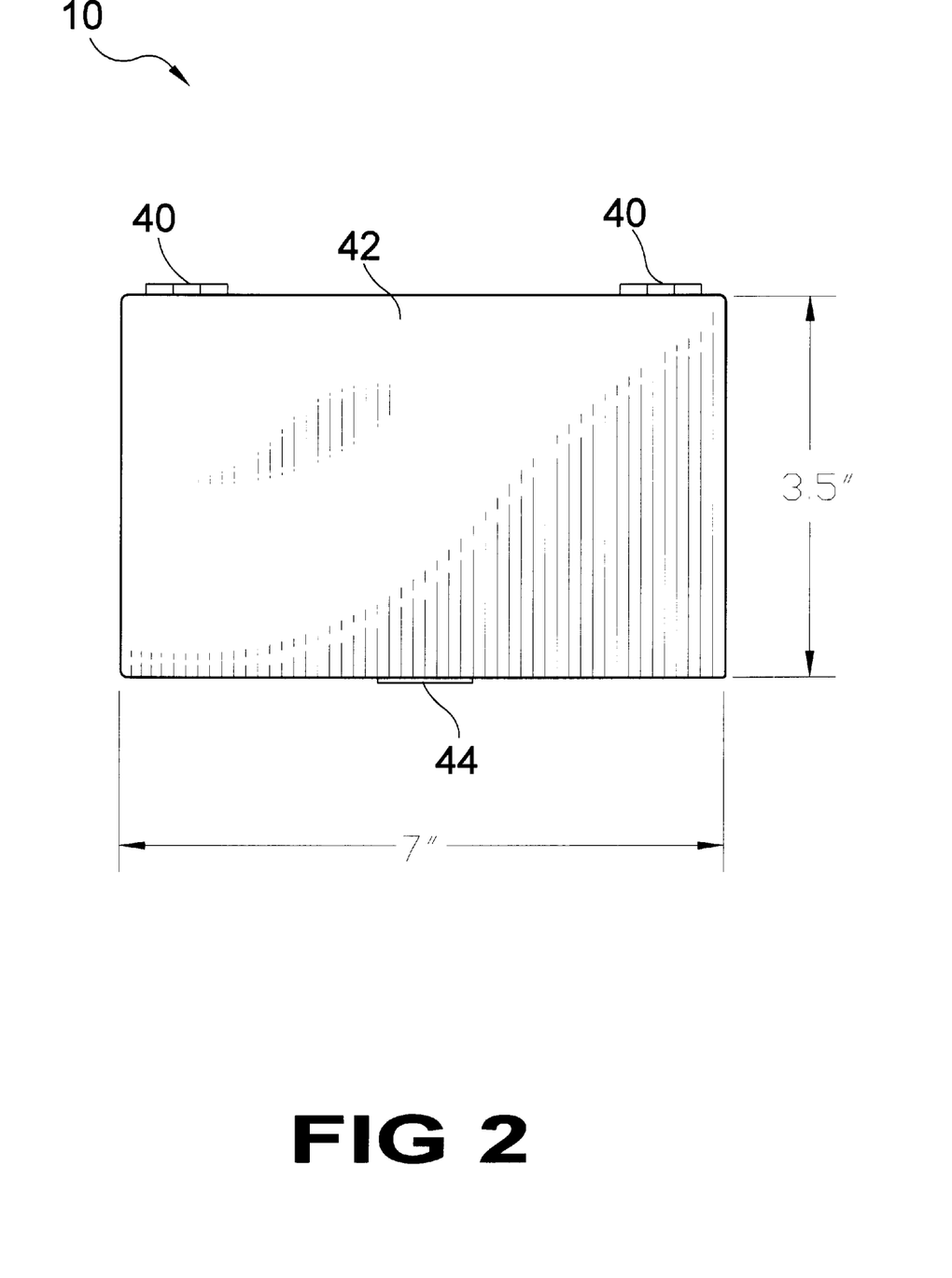
FIG. 2 is a top perspective view of the hand-held computer of the present invention in a closed position.

A top view of the hand-held computer 10 is illustrated in FIG. 2. From this view the top side 42 of the hand-held computer 10 is clearly seen. Positioned on one side of the hand-held computer 10 between the top and bottom sides 12 and 14, respectively, are hinges 40. The hinges 40 pivotally connect the top side 12 to the bottom side 14. On a side of the hand-held computer 10 opposite the hinges 40 is the clasp 44. The clasp 44 selectively locks the top side 12 to the bottom side 14 and prevents pivotal movement of the top side 12. Locking of the clasp 44 also prevents access to the display screen 16 and the function keys.

Figure 3:
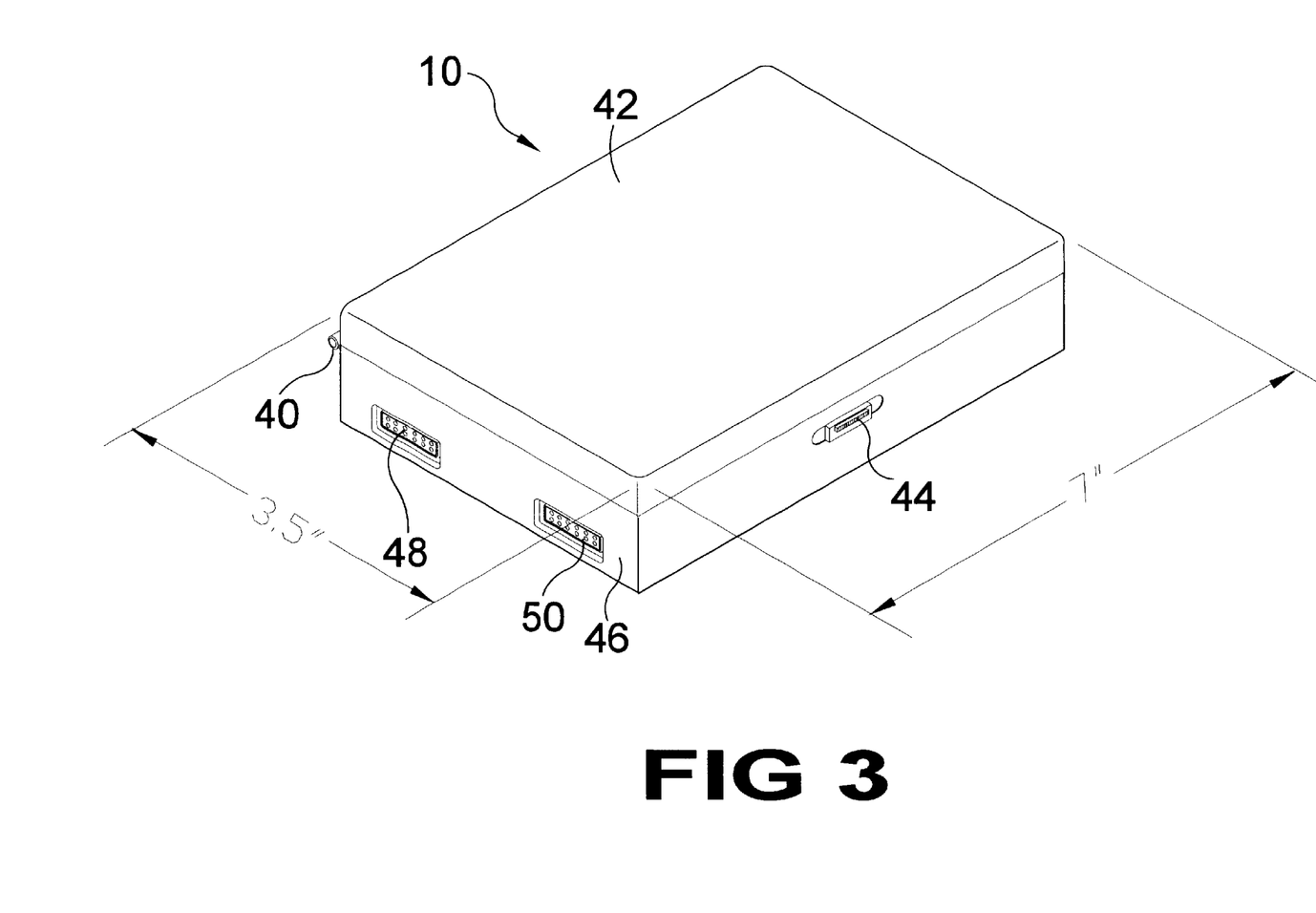
FIG. 3 is left side view of the hand-held computer of the present invention.

A left side perspective view of the hand-held computer 10 is illustrated in FIG. 3. From this view a left side 46 of the hand-held computer 10 is visible. Positioned on the left side 46 is a first peripheral device port 48 for connection of a first peripheral device such as a computer for transferring data to the hand-held computer 10. Also positioned on the left side 46 is a second peripheral device port 50 for connection of a second peripheral device such as a printer for generating a hard copy of data stored within the hand-held computer 10. The first peripheral device port 48 is preferably a serial port for transmitting data serially and the second peripheral device port 50 is preferably a parallel port for transmitting data in parallel. However, the first and second peripheral device ports 48 and 50, respectively, may be any combination of serial and parallel ports desired for user specific operation of the hand-held computer 10 and the present invention is not meant to be limited to the installation of one serial and one parallel peripheral device port.

Figure 4:
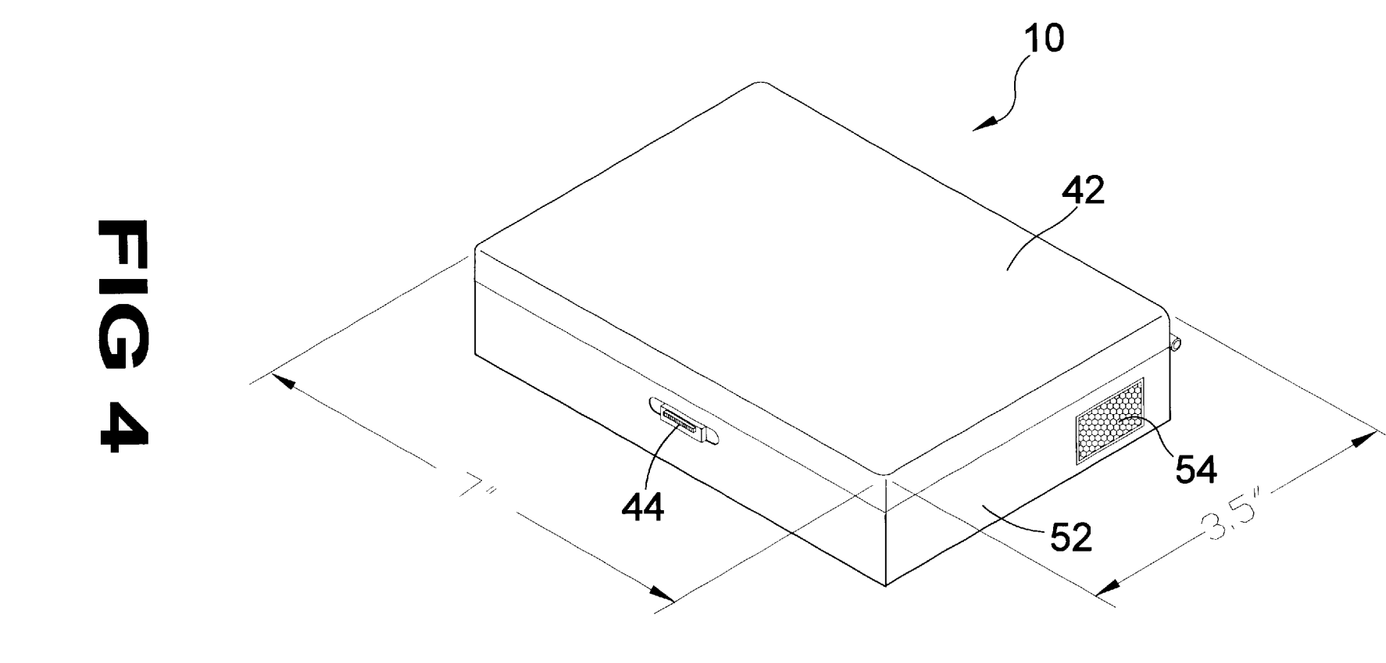
FIG. 4 is a fight side view of the hand-held computer of the present invention.

A right side view of the hand-held computer 10 is illustrated in FIG. 4. From this view, the speaker 54 is shown positioned on a right side 52 of the hand-held computer 10. As discussed hereinbefore, the speaker 54 is provided for generating audible signals to alert the user as to a particular situation. These audible signals include an audible alarm signal for alerting the user when it is time to take medications, nutritional supplements, minerals/nutrients, homeopathic medications. The speaker 54 also creates an audible alarm signal to alert the user when any combination of medication, nutritional supplements/nutrients, homeopathic medicines and minerals and may cause an interaction. Also audiblized through the speaker 54 are messages of encouragement and support to the user.

Figure 5:
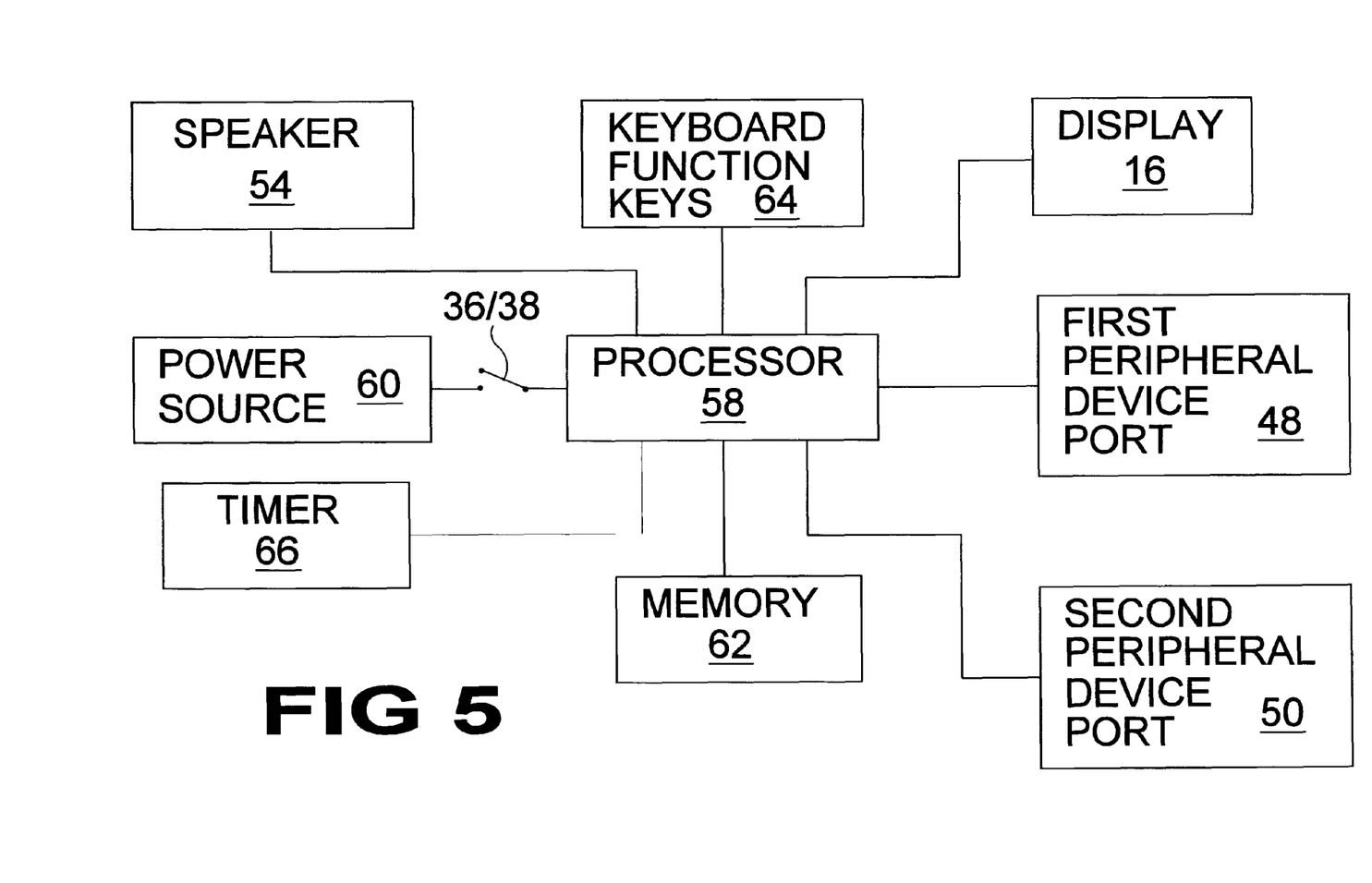
FIG. 5 is a block diagram of the hand-held computer of the present invention showing the internal components therein.

A block diagram of the hand-held computer 10 is illustrated in FIG. 5. As can be seen from this view, the hand-held computer 10 includes a processor 58. The processor 58 is connected to a source of power 60 through the on and off buttons 36 and 38. A memory 62 is provided for storing the application programs used by the hand-held computer 10, information data regarding drugs, nutritional supplements or nutrients, minerals and companies that produce these products and individual patient profiles input by a user of the hand-held computer 10. The keyboard function keys 64 are also connected to the processor 58 for use in inputting data. The display 16 is connected to the processor 58 for displaying information requested by the user, application menus for aiding the user in obtaining information and data input to the hand-held computer 10 by the user. The first and second peripheral device ports 48 and 50, respectively, are provided to connect peripheral devices to the processor 58 to allow for the input and output of data. The processor 58 monitors the power of the power source 60 and indicates a low power level on the display screen 16 thereby notifying the user that the power source needs to be replaced or charged. A timer 66 is also connected to the processor 58 for tracking the time and date for use by the processor to alert the user as to the proper time to ingest drugs, supplements or nutrients and minerals that have been programmed therein. The processor 58 further uses the timer 66 for controlling the contrast and brightness at which information is displayed on the display screen 16. The timer is also connected to the processor 58 for tracking the user's personal schedule; daily, weekly, monthly, that has been programmed therein. The speaker 54 is also connected to and controlled by the processor 58 to generate audible alarm signals.

The operation of the hand-held computer 10 will now be described with reference to the figures. In operation, the hand-held computer 10 is able to perform a number of applications as will be discussed hereinbelow with specific reference to the flow charts illustrated in FIGS. 6–10.

The hand-held computer 10 includes the memory 62 which is preprogrammed to store a plurality of application programs as well as data. The data preprogrammed into the memory 62 includes information concerning numerous drugs, nutritional supplements, minerals and nutrients as well as drug and nutritional supplement companies. The data concerning the drugs, nutritional supplements, nutrients and minerals includes the main ingredients, information on how and when to take the drugs, nutritional supplements, minerals and nutrients and information on interactions of individual drugs, nutritional supplements, minerals and nutrients with other types of drugs, nutritional supplements, minerals and nutrients. The data concerning the drugs, nutritional supplements, nutrients and minerals also includes clinical pharmacology, clinical studies, contraindications; warnings, precautions, adverse reactions, dosages; administration; how supplied, animal toxicology; patient information, cautions, side effects and any nutrient or mineral interactions.

The information concerning the drug and nutritional supplement companies includes information regarding the company, the products produced by the company and the tradenames for the different products produced. Information is updated in the memory 62 via connection with a peripheral device such as a computer through one of the peripheral device ports 48 or 50. The information is updated and saved in the memory 62 using an application stored in the memory as will be discussed hereinafter. The applications programs stored in the memory 62 include an individualization program for collecting individual, personal data regarding the user and a time management program for keeping track of the current day and time and is used by other applications for managing operation thereof. An intake monitoring program is stored in the memory 62 for monitoring the user's intake of medication, nutritional supplements, nutrients and minerals via an interactive program along with an intake scheduling program for programming a schedule for taking medication, nutritional supplements, nutrients and minerals to be followed by the intake monitoring program. An intake analysis program is also stored in the memory 62 for tracking data regarding the intake of medication, nutritional supplements, nutrients and minerals by a user over a period of time. An intake guidance and safeguard program is provided for interactive use to guide the user in taking the proper dosage of medications, nutritional supplements, nutrients and minerals to prevent harmful interactions therebetween. A verification program is a user interactive program stored in the memory 62 for verifying a dosage of medication, nutritional supplements, nutrients and minerals, e.g., the verification program verifies that the data related to dosage is correct. An intake feedback program is stored in the memory 62 for reviewing the progress of the user in taking medications, nutritional supplements, nutrients and minerals and provides positive feedback through the speaker 54 to encourage the user to continue taking medications, nutritional supplements, nutrients and minerals as required. Upon activation of the on button 36, the hand-held device 10 will be activated and the processor 58 will "boot up" and display a main menu on the display screen 16. The main menu contains options for activating any of the plurality of programs stored in the memory 62.

Figure 6:
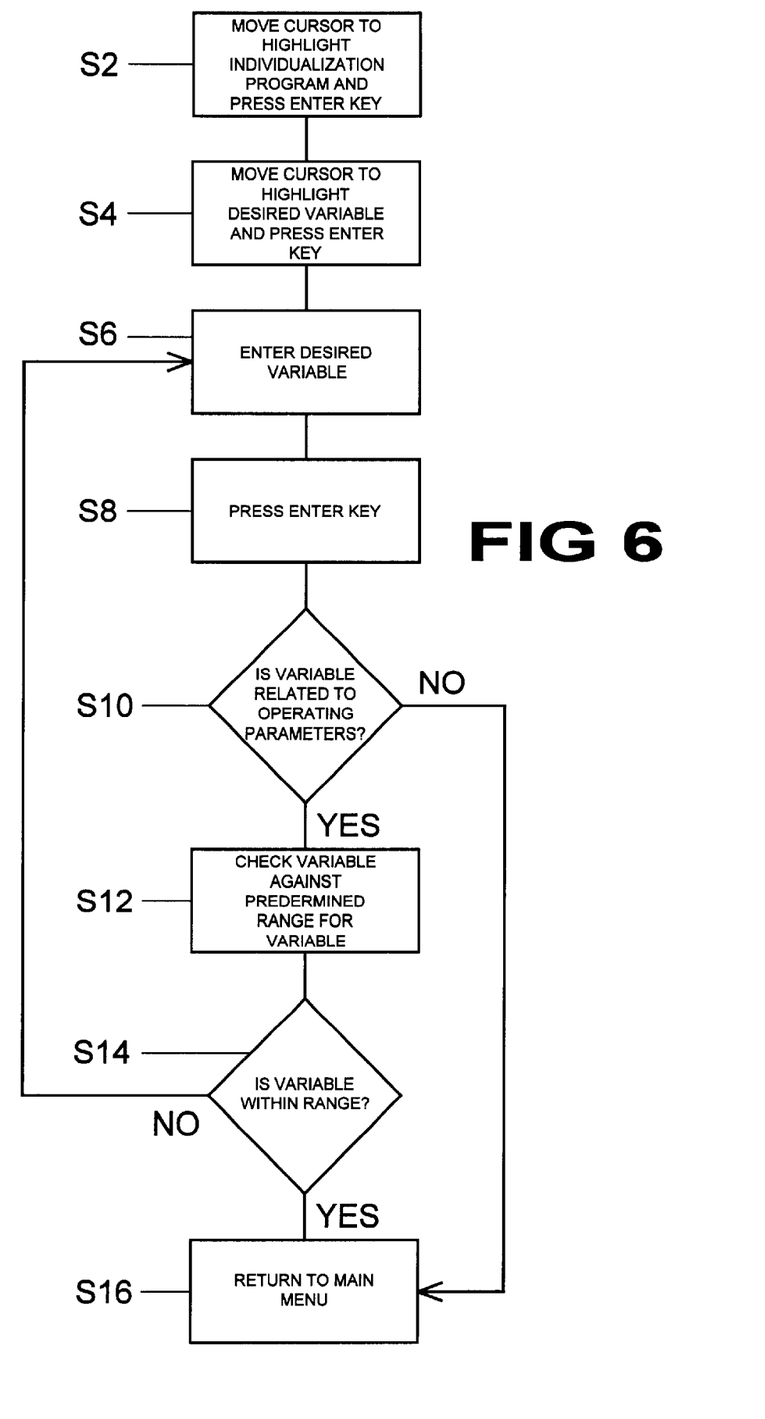
FIG. 6 is a flow chart of the application for entering individualized data for each patient or user and data related to the functioning of the processor.

The flow chart of FIG. 6 illustrates the steps performed during the individualization program. This application program is used for collection of general data regarding a user such as name, medical record number, date of birth, type of medication, nutritional supplements, nutrients and minerals, dosages and times at which medication, nutritional supplements, nutrients or minerals are to be taken and personal scheduling. This application is also used to set a security pass code if desired to provide restricted access to the data and other data necessary for the functioning of the hand-held computer 10. A main menu is provided as a default screen on the display screen 16 which includes a selection for starting the individualization program.

In order to start the individualization program the user moves the cursor using the appropriate function keys until the selection for the individualization program is highlighted and presses an enter key 68 as discussed in step S2. This will load the individualization program into the processor 58 and provide the user with a secondary menu requesting the variable to be entered. These variables include name, medical record number, date of birth, dosages, type of medication, nutrient or mineral and times at which medication, nutritional supplements, nutrients or minerals are to be taken, a personal scheduling function, date and time of the timer 66 and a security pass code. The user will again move the cursor using the appropriate function keys to highlight a desired variable to be set and press the enter key 68 as stated in step S4. The user is now prompted to enter the desired variable and enters the variable using the alphanumeric keyboard 34 and numerical keyboard 26 as described in step S6. Upon completion of the entry of the variable the user presses the enter key 68 to input and store the variable in a desired location in the memory 62 as discussed in step S8.

If the user is entering a variable related to the functioning of the processor 58, the processor 58 will determine such as stated in step S10. If the processor 58 determines that the variable is not related to the functioning of the processor 58 the application is returned to the main menu in step S16. If it is determined that the variable entered is related to the functioning of the processor 58, the processor 58 compares the entered variable to a predetermined range for the variable as described in step S12. The processor 58 then determines if the variable is within the range as discussed in step S14. If the variable is not within the range then the application is returned to step S6 wherein the user is prompted to and reenters the variable. If the variable is within the predetermined range then the application returns to the main menu as stated in step S14.

Figure 7:
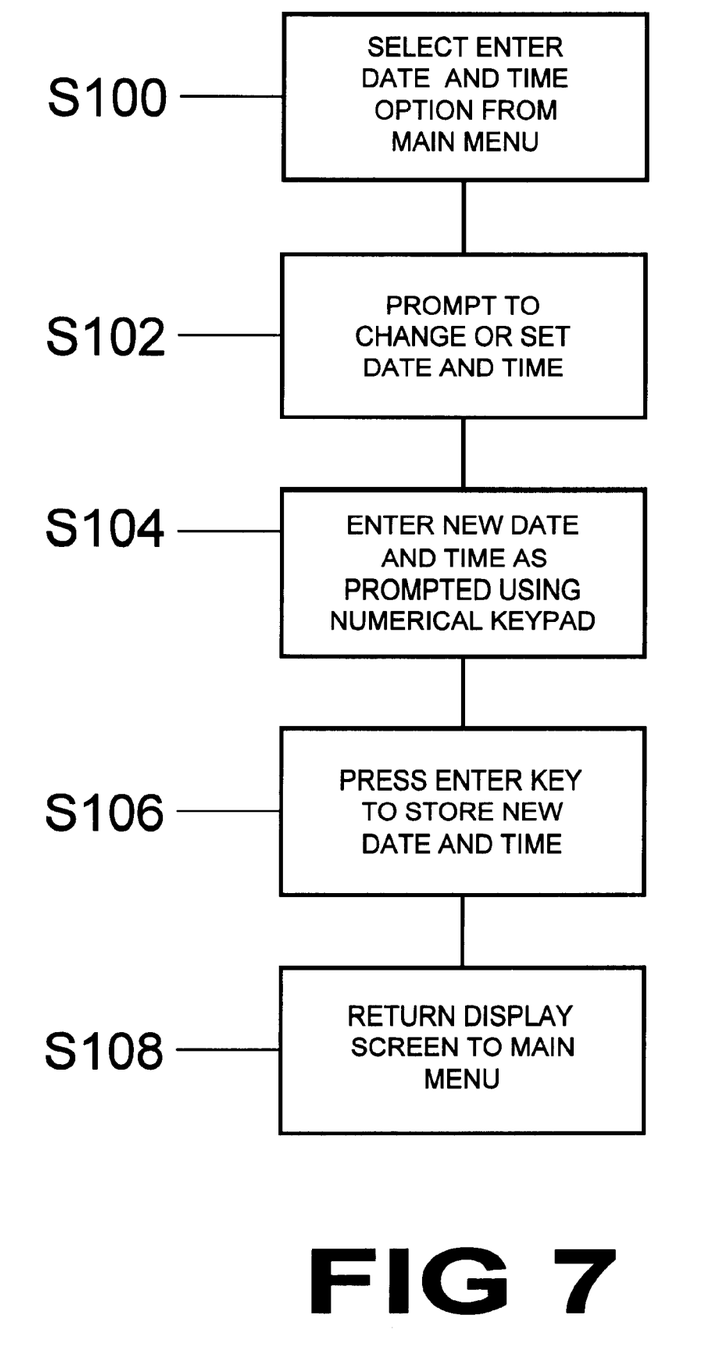
FIG. 7 is a flow chart of the time management application for monitoring the schedule of the patient or user.

FIG. 7 illustrates a flow chart of the time management application for monitoring the schedule of the user. In order to activate this application the user will select the time management option on the main menu as discussed in step S100. This program is used to set and maintain the date and time to be monitored by the processor 58 and is used by other programs to match the actual time and date with stored times and dates. Once set, the date and time will be constantly displayed on the display screen 16. Upon selection of the time management option, the user is prompted to change or set a new date and time as stated in step S102. In response to this prompt, the user will use the numerical keyboard to enter a new date and time in accordance with the prompts provided on the display screen 16 as described in step S 104. Upon completing the entry of the new date and time, the user will press the enter key 68 to store the new date and time as discussed in step S106. The processor 58 will now operate based upon the newly entered date and time and return the display to show the main menu as stated in step S108.

Figure 8:
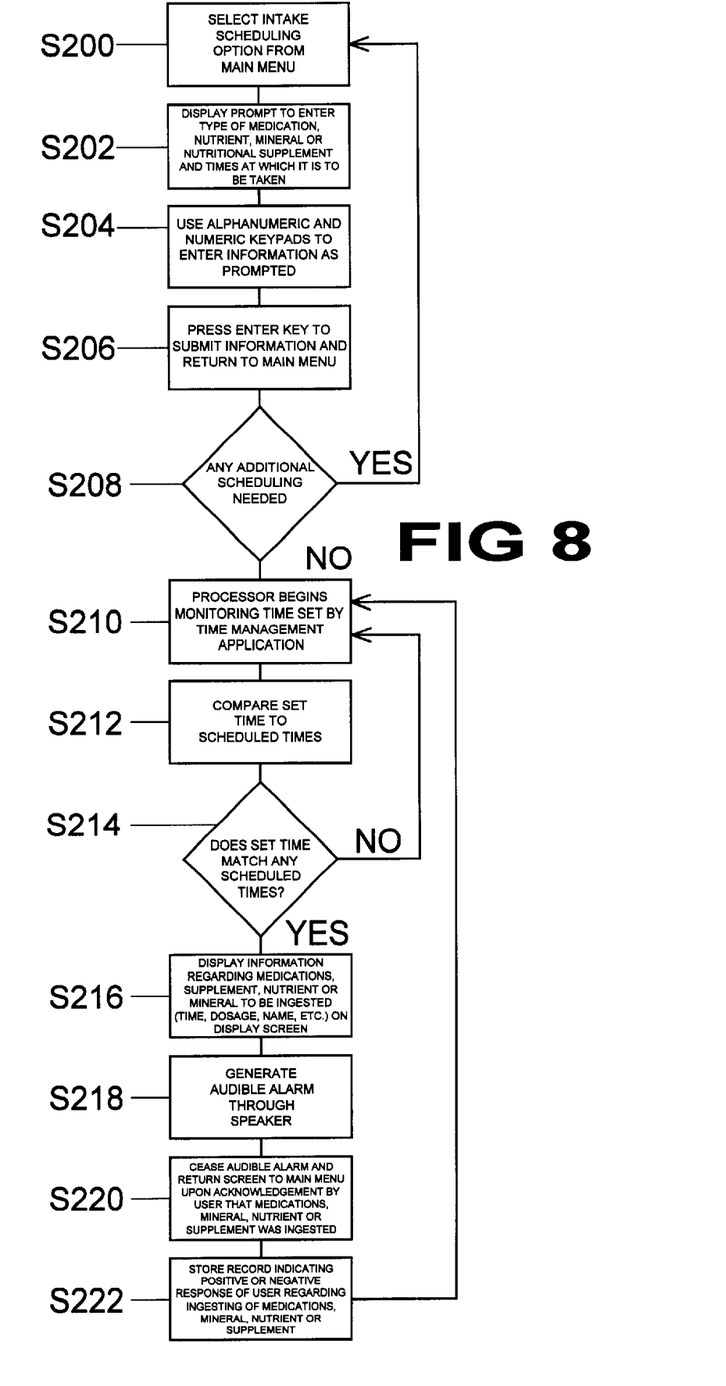
FIG. 8 is a flow chart of the application for scheduling and monitoring the drug, nutritional supplement/nutrient and mineral intake of the patient or user.

The intake scheduling and monitoring program is provided for scheduling the user's intake of medications, daily, weekly or monthly activities and nutrients, minerals and nutritional supplements for storage and monitoring by the processor 58 and monitoring when the user is to be notified that it is time to ingest the scheduled medications, nutrients, minerals and nutritional supplements and when to carry out an activity. FIG. 8 illustrates a flow chart showing the process followed by the hand-held device 10 to perform the intake scheduling function and monitoring the schedule to alert the user as to the proper times for ingesting medications, nutrients, minerals and nutritional supplements or carrying out an activity.

The user must first schedule when it is time to take medications, nutrients, minerals and nutritional supplements. The user will activate the intake scheduling application by selecting the intake scheduling option from the main menu as discussed in step S200. This causes a prompt to enter information about the medications, nutrients, minerals and nutritional supplements and the time at which they are to be taken to be displayed as stated in step S202. The user then uses the alphanumeric and numeric keypads to enter the information to the hand-held device 10 based upon the prompts displayed as described in step S204. Upon completing entry of the information as prompted, the user presses the enter key 68 to submit the information to the memory 62 for monitoring by the processor 58 as discussed in step S206. The processor 58 then returns the display to show the main menu. The user must now determine if any additional scheduling is desired as described in step S208. If additional scheduling is desired for another medications, nutrients, minerals and nutritional supplements, the user will repeat the steps discussed above starting with step S200.

If no additional scheduling is needed, the processor begins to monitor the time set by the time management application as stated in step S210. The processor 58 constantly compares the set time to the time for ingesting medications, nutrients, minerals and nutritional supplements set during the scheduling portion of the application (steps S200–S208). The comparison of the set time and date with the scheduled times and dates is performed in step S212. The processor 58 then determines whether the set time matches any of the scheduled times stored in the memory 62 in step S214. If the processor 58 determines that the set time and any of the scheduled times do not match, the application is returned to step S210 and the processor 58 continues to monitor the set time.

Upon determining that the set time matches one of the scheduled times, the processor 58 activates the display screen 16 to display information concerning the scheduled medications, nutrients, minerals and nutritional supplements, the dosage amount and the time at which the dosage should be ingested as stated in step S216. The display also provides a prompt regarding whether the medications, nutrients, minerals and nutritional supplements were ingested. The user then answers the prompt with a positive or negative response and enters the dosage taken. The processor 58 also generates an audible alarm through the speaker 54 to audibly alert the user that it is time to ingest medications, nutrients, minerals or nutritional supplements as discussed in step S218. Upon the user responding to the prompt on the display screen 16 indicating whether the medications, nutrients, minerals or nutritional supplements were ingested, the processor turns off the audible alarm and the display screen is returned to the main menu as described in step S220. The response of the user is then stored in memory 62 to provide a record of whether the user is ingesting the scheduled dosages of medications, nutrients, minerals and nutritional supplements at the scheduled times as stated in step S222 and the application returns to step S210. The processor continues to monitor the set time for comparison with the scheduled times to alert the user when the next scheduled time to ingest medications, nutrients, minerals or nutritional supplements arrives.

Figure 9:
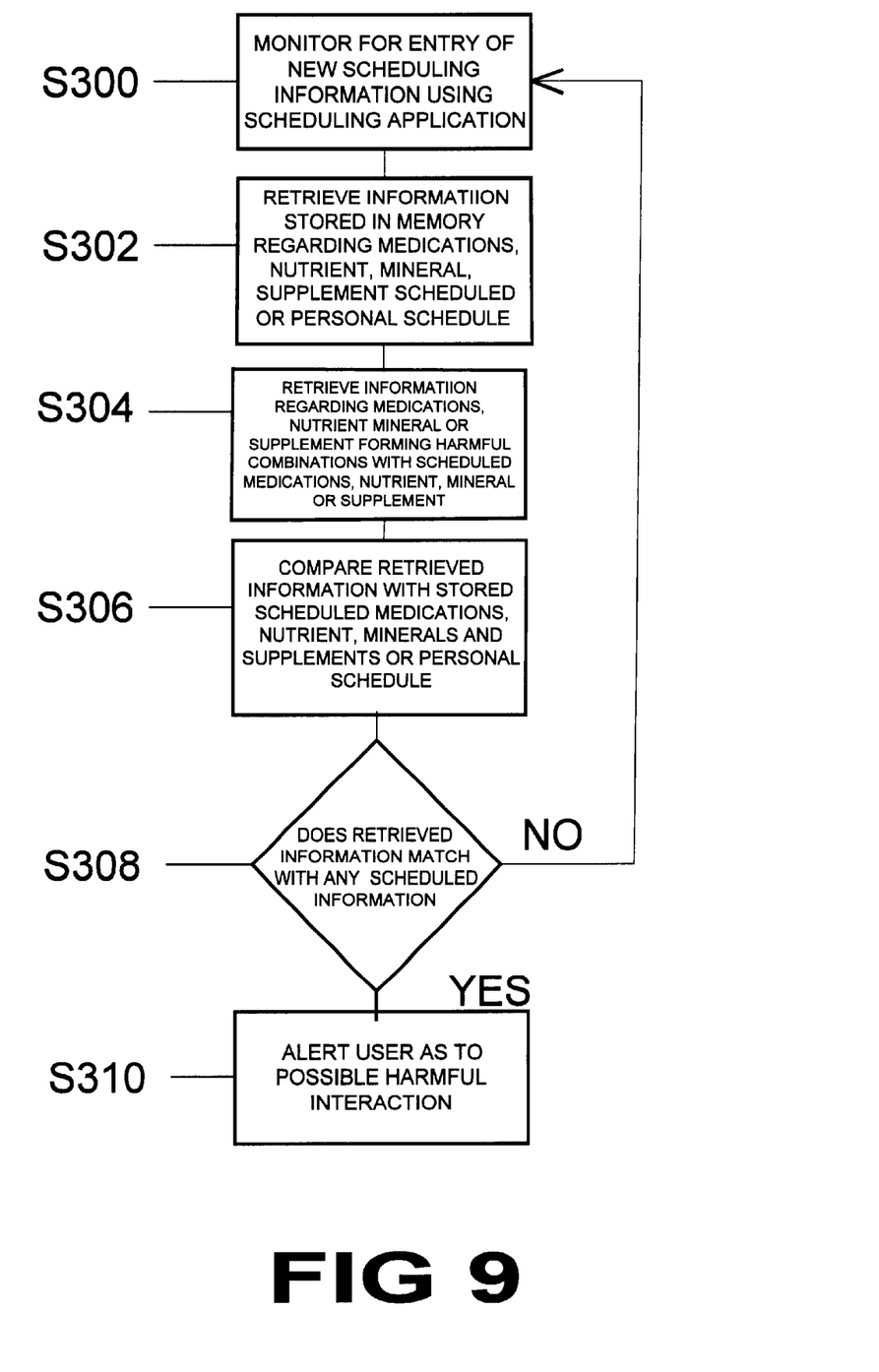
FIG. 9 is a flow chart of the interactive application for guiding and safeguarding the drug, nutritional supplement/nutrient and mineral intake of the patient or user.

An intake guidance and safeguard program is also stored in memory 62 for alerting the user as to harmful interactions of medications, nutrients, minerals and nutritional supplements scheduled by the user. A flow chart illustrating the process followed by this application is shown in FIG. 9. The intake guidance and safeguard application constantly monitors the entering of new scheduling information by following the process of the intake scheduling application described above and illustrated in the flow chart of FIG. 8 as discussed in step S300. Upon entry of the medications, nutrients, minerals or nutritional supplements for scheduling, the processor 58 retrieves information concerning the scheduled medications, nutrients, minerals, nutritional supplements, or a personal schedule as stated in step S302. From the retrieved information the processor 58 analyzes the information concerning medications, nutrients, minerals and nutritional supplements which cause harmful combinations with the newly scheduled medications, nutrients, minerals or nutritional supplements as described in step S304. The analyzed information is now compared to previously stored scheduled information on medications, nutrients, minerals or supplements or personal schedules as discussed in step S306. The processor 58 then makes a determination based upon the comparison as to whether any of the medications, nutrients, minerals and nutritional supplements determined to cause a harmful combination with the newly scheduled medications, nutrients, minerals or nutritional supplements have been scheduled for ingestion by the user as described in step S308. If there are no matches found, the application returns to step S300 and continues to monitor for new schedule entries. If a match is found, the processor 58 generates an audible signal through the speaker 54 and provide a message on the display screen 16 to alert the user as to the possible harmful interaction as discussed in step S310.

Figure 10:
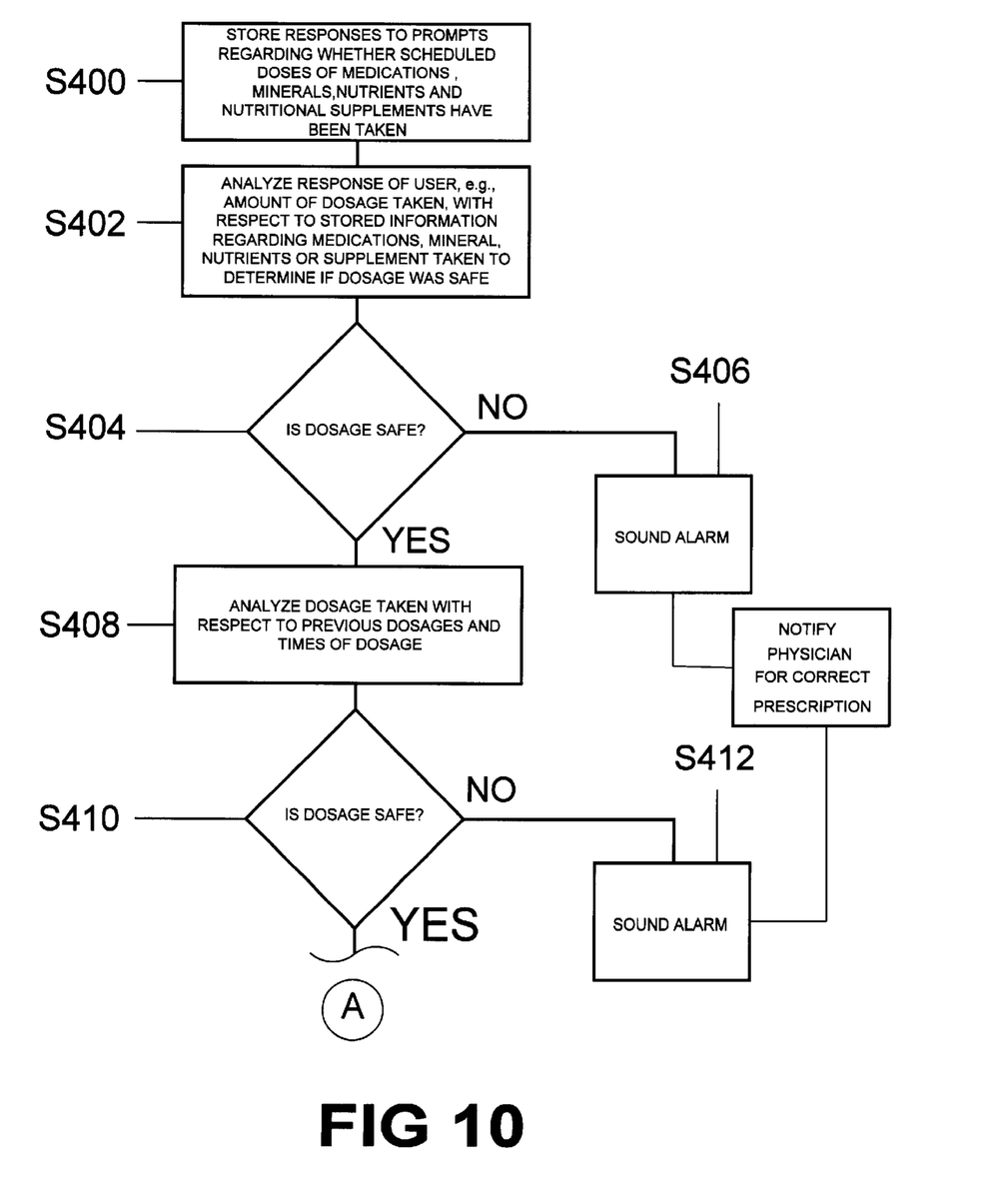
FIG. 10 is a flow chart of the application for analyzing and recording the drug, nutritional supplement/nutrient and mineral intake of the patient or user.

The hand-held device 10 also maintains a record of responses made by the user when prompted to take scheduled doses of medications, nutrients, minerals and nutritional supplements in an intake analysis program. A flow chart illustrating the process followed by the intake analysis program is shown in FIG. 10. The intake analysis program constantly monitors information input by the user in response to prompts by the hand-held device 10 that it is time to take scheduled medications, nutrients, minerals and nutritional supplements. Upon input of a response to the prompts provided on the display screen, the information is stored in the memory 62 as discussed in step S400. The processor 58 then analyzes the information stored in the memory 62 to determine if the user has taken a safe dose of the scheduled medications, nutrients, minerals and nutritional supplements as stated in step S402. The analysis consists of a comparison of the dosage input by the user with safety guidelines regarding the scheduled medications, nutrients, minerals and nutritional supplements. It is then determined whether the dosage taken is unsafe in step S404. If the dosage taken is determined to be unsafe then the processor 58 generates an audible alarm signal to alert the user that medical assistance should be alerted as described in step S406. If the dosage taken is determined to be a safe amount then the analysis continues at step S408. The dosage taken is then analyzed with respect to previously stored responses of the user regarding the dosages taken and the times at which the dosages were taken to determine if the present dose amount was safe as described in step S408. It is then determined whether the dosage taken is unsafe in step S410. If the dosage taken is determined to be unsafe then the processor 58 generates an audible alarm signal to alert the user that medical assistance should be obtained as described in step S412. If the dosage taken is determined to be a safe amount then the analysis continues at step S414.

Upon determining that the dosage taken was of a safe level, the processor 58 then analyzes the information stored therein to determine certain information regarding the daily and weekly intake of medications, nutrients, minerals and nutritional supplements for the user as stated in step S414. Examples of the statistics determined include average daily and weekly intake of medications, nutrients, minerals and nutritional supplements by the user and generate charts of daily, weekly and monthly usage for output to a peripheral device such as a printer. After generation of the statistics, the processor 58 analyzes the statistics to generate and provide recommendations for future intake of the medications, nutrients, minerals and nutritional supplements as discussed in step S416. The processor 58 also determines statistics regarding the amount of variation by the user from the scheduled routine of ingesting medications, nutrients, minerals and nutritional supplements as stated in step S418. A determination is then made based upon the statistics regarding the amount of variation by the user from the scheduled routine of ingesting medications, nutrients, minerals and nutritional supplements as to whether the user follows the schedule strictly or varies more than a predetermined amount as described in step S420. The processor 58 also analyzes the statistics regarding the amount of variation by the user from the scheduled routine of ingesting medications, nutrients, minerals and nutritional supplements and if the user varies the scheduled routine by less than a predetermined amount generates audible messages of congratulations as discussed in step S422. The messages of words of encouragement are provided through the speaker 54 to encourage the user to continue following the schedule. If it is determined in step S420 that the user varies from the scheduled routine by more than a predetermined amount this generates audible messages of recommendation to seek medical advice as discussed in step S424. The messages of recommendation to seek medical attention are provided through the speaker 54 to encourage the user to follow the schedule more strictly.

When all of these programs are operating, the user is able to input a schedule of ingestion of medications, nutrients, supplements and minerals to follow. The user is thus provided assistance in maintaining a diet and regimen for taking medications, minerals and nutritional supplements or nutrients. The hand-held device 10 that is programmable to store a plurality of data blocks including time and date stamps and monitor an internal clock to determine when the time and date stamp of each block of information matches the time of the clock. The data relates to information concerning a time schedule for a user to ingest medications, minerals, nutritional supplements and nutrients and appropriate dosage amounts. The hand-held device notifies the user at the appropriate time via visual and audible alarms that a particular medication, nutrient, nutritional supplement or mineral is scheduled to be ingested and informs the user of the correct dosage or amount.

The hand-held device also stores a large amount of information regarding different medications, nutrients, nutritional supplements or minerals including information on certain medications, nutrients, nutritional supplements or minerals which produce harmful interactions/effects and dosage amounts which may produce harmful interactions/effects and those dosage amounts considered safe. Upon entering schedule information, the processor of the hand-held device 10 compares the information input thereto with the stored information regarding prescribed medications, nutrients, nutritional supplements, and minerals and other scheduled information previously stored. The processor 58 determines from the stored and input information whether the dosage entered or the combination of the medications, nutrients, nutritional supplements or minerals entered with another medications, nutrients, nutritional supplements or minerals previously entered will cause an interaction. The user is also able to retrieve the stored information by activation of an appropriate function key. By activation of the prescription key, nutritional supplement key, homeopathic drug key and nutrient/mineral key the user can obtain information on any drug, nutritional supplement and nutrient/mineral which is stored in the memory 62. The user is also able to obtain information on any drug company or nutritional supplement company by pressing either the drug company key 30 or nutritional supplement company key 32 and entering the name of the desired company using the alphanumeric keypad 34. By selecting the user information option on the main menu and pressing the medical record number key 28, the user can obtain any stored information on a patient identified by an entered medical record number.

First and second peripheral device ports are provided on the hand-held device 10 for connecting peripheral devices to the processor 58. The processor is thus able to be updated with information from a second computer or an externally connected disk drive to provide the hand-held device with the latest scientific and research information concerning drugs, nutrients, nutritional supplements or minerals and to provide additional information not already stored therein. A second peripheral device such as a printer may be connected to the processor through the second peripheral device port for receiving information from the processor and producing a hard copy of the information.

From the above description it can be seen that the hand-held computer of the present invention is able to overcome the shortcomings of prior art devices by providing a hand-held computer which is able to store information regarding known allopathic and homeopathic pharmaceutical drugs, individual effects, properties, recommendations for use and effects when combined with nutritional supplements, minerals and/or nutrients, this information being provided to a user on demand. The hand-held computer is also able to store information concerning nutrients found in foods and nutritional supplements and providing such information to a user on demand as well as medical and nutritional information concerning individuals may be stored for use in forming a nutritional and drug profile for the individual. The hand-held computer includes a processor which is able to analyze the drug and nutritional information with respect to medical information concerning an individual in order to provide a user with alternative drug, nutrient or mineral recommendations and a memory for storing information concerning producers and manufacturers of allopathic and homeopathic drugs, nutritional supplements, minerals and nutrients. A first peripheral input port is provided for connecting a peripheral device and thereby updating information stored in the memory and a second peripheral port is provided for connecting with a printer or other output device and producing a hard copy of information provided to a user.

The memory of the hand-held computer includes a database stored therein of known pharmaceutical and homeopathic drug companies, a listing of their respective drugs and a description of each drug, the description of each drug including its generic name, common uses, cautions, clinical pharmacology, clinical studies, contraindications; warnings, precautions, adverse reactions, dosages; administration; how supplied, animal toxicology; patient information, cautions, side effects and any nutrient or mineral interactions, side effects and any nutrient or mineral interactions, a database of known nutritional supplement companies, their respective supplements and a description of each supplement, the description including cautions regarding the supplement, side effects and any drug interactions and a complete database of nutrients and minerals and the recommended daily intakes for men, women and children for each. The hand-held computer also includes a drug and nutrient interaction program stored therein for providing the user with the best possible information regarding the interactions of any drug with any nutrient. Furthermore, the hand-held computer of the present invention is simple and easy to use and economical in cost to manufacture.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A hand-held computer for alerting a user when scheduled medications, nutritional supplements, minerals and nutrients should be ingested, said computer comprising:

a) a housing having a face side;

b) a processor positioned inside said housing;

c) a memory unit connected to said processor for storing user input data concerning a schedule for ingesting desired medication, nutritional supplements, minerals and nutrients, and information concerning medications, nutritional supplements, nutrients and minerals which form harmful combinations;

d) a display screen positioned on said face side of said housing for displaying a message from said processor related to the schedule for ingesting desired medications, nutritional supplements, minerals and nutrients;

e) function keys connected to said processor for inputting the data concerning the schedule for ingesting desired medications, nutritional supplements, minerals and nutrients, wherein said data includes a signal identifying the desired medications, nutritional supplements, minerals and nutrients to be ingested and a time at which said medications, nutritional supplements, minerals and nutrients is to be ingested and said processor monitors a time of day and alerts the user when a scheduled time for ingesting said medications, nutritional supplements, minerals and nutrients arrives;

f) said processor comparing data entered by the user with said data regarding medications, nutritional supplements, nutrients and minerals to determine if the user has scheduled a harmful combination of medications, nutritional supplements, nutrients and minerals; and g) said function keys include a drug company key and a nutritional supplement company key and said memory stores data regarding numerous drug companies and nutritional supplement companies and wherein activation of one of said drug company keys and nutritional supplement company keys provides the user with data regarding a desired medication, nutritional supplement, nutrient and mineral.

2. The hand-held computer as recited in claim 1, further comprising a speaker connected to said processor for generating an audible alarm signal and alerting the user when a scheduled time for ingesting said medications, nutritional supplements, minerals and nutrients arrives.

3. The hand-held computer as recited in claim 1, further comprising a first peripheral port for connection of a peripheral device to said processor for inputting data to said processor.

4. The hand-held computer as recited in claim 1, further comprising a second peripheral port for connection of a second peripheral device to said processor for outputting data from said processor.

5. The hand-held computer as recited in claim 1, wherein said function keys include a prescription drug key, a nutritional supplement key, a homeopathic drug key and a nutrient/mineral key and said memory stores data regarding numerous medications, nutritional supplements, nutrients and minerals and wherein activation of one of said prescription drug key, nutritional supplement key, homeopathic drug key and nutrient/mineral key provides the user with data regarding a desired medication, nutritional supplement, nutrient or mineral.

6. The hand-held computer as recited in claim 5, wherein said function keys further include an alphanumeric keyboard for inputting a medications, nutritional supplements, nutrients and minerals for which data is desired.

7. The hand-held computer as recited in claim 2, wherein said processor ceases generation of said audible alarm signal upon receipt of response data from said user indicating whether the user ingested the scheduled medications, nutritional supplements, nutrients and minerals.

8. The hand-held computer as recited in claim 7, wherein said processor further calculates statistics regarding the frequency the user ingests scheduled medication based upon said response data.

9. The hand-held computer as recited in claim 8, wherein said processor causes said speaker to generate an audible message of recommendation when said statistics indicate that the frequency that the user ingests scheduled medication, nutritional supplements, nutrients and minerals is below a predetermined threshold level.

10. The hand-held computer as recited in claim 8, wherein said processor causes said speaker to generate an audible message of recommendation when said statistics indicate that the frequency that the user ingests scheduled medication, nutritional supplements, nutrients and minerals is above a predetermined threshold level.

11. The hand-held computer as recited in claim 1, wherein said housing further comprises a top side and a bottom side pivotally connected together and movable between a first closed position restricting access to said function keys and a second open position permitting access to said function keys.

12. The hand-held computer as recited in claim 11, further comprising a clasp for selectively securing said top and bottom sides in said first closed position.

13. The hand-held computer as recited in claim 1, wherein said function keys further include an alphanumeric keyboard for inputting a drug company or nutritional supplement company for which data is desired.

14. The hand-held computer as recited in claim 1, wherein said data regarding a schedule is stored for a plurality of users, each user being assigned a unique medical record number and said function keys include a medical records number key wherein activation of said medical record number key allows a user to obtain data stored on a desired patient.

15. The hand-held computer as recited in claim 14, wherein said function keys also includes a numerical keypad for use in inputting a numerical record number of a patient of which data is desired.

* * * * *